United States Patent [19]

Sato et al.

[11] Patent Number: 4,832,954
[45] Date of Patent: May 23, 1989

[54] NICORANDIL CONTAINING EXTERNAL PREPARATIONS

[75] Inventors: Kiyoshi Sato, Tsurugashima; Yasunori Morimoto; Kenji Sugibayashi, both of Sakado; Masao Ueno, Tokorozawa, all of Japan

[73] Assignee: Nisshin Flour Milling Co., Ltd., Japan

[21] Appl. No.: 86,575

[22] Filed: Aug. 17, 1987

[30] Foreign Application Priority Data

Aug. 22, 1986 [JP] Japan ................. 61-195508

[51] Int. Cl.$^4$ .............................................. A61L 15/03
[52] U.S. Cl. ...................................... 424/449; 514/355; 514/946; 514/947
[58] Field of Search ............... 424/449; 514/355, 946, 514/947

[56] References Cited

U.S. PATENT DOCUMENTS 4,200,640  4/1980  Nagano et al. ................... 514/355
4,769,381  9/1988  Ishihara et al. .................. 514/355

OTHER PUBLICATIONS

Kamiyama et al., CA. 106:201753d (1987), of Jpn. 6236317, Feb. 17, 1987.
Kuroodo et al., CA. 105:49085g (1986), of Jpn. 6178720, Apr. 22, 1986.

*Primary Examiner*—Shep K. Rose
*Attorney, Agent, or Firm*—Abelman Frayne Rezac & Schwab

[57] ABSTRACT

The transdermal penetration of N-(2-hydroxyethyl) nicotinamide nitrate useful for the treatment of angina pectoris is improved by the use of a mixed solvent comprising an alcohol of 2 to 7 carbon atoms and an aliphatic ester having a molecular weight of at least 180 in the formulation of the external preparations.

7 Claims, No Drawings

NICORANDIL CONTAINING EXTERNAL PREPARATIONS

FIELD OF THE INVENTION

This invention relates to external preparations comprising N-(2-hydroxyethyl)nicotinamide nitrate as an active ingredient.

PRIOR ART OF THE INVENTION

Heretofore, nitrous acid preparations such as nitroglycerin, (β-blockers such as Pindolol and Propranolol, and Ca antagonists such as Nifedipin are well known as drugs for use in the treatment of angina pectoris. Although the above-mentioned drugs, most of which have been formulated into oral dosage forms, are effective as a remedy against a sudden attack of angina pectoris, they were not found appropriate as preventives for the reasons that they produce adverse side-effects, thus not permitting their abuse.

In recent years, keeping pace with the development of external preparations for nitroglycerin and isosorbide nitrate, an attempt has been made to be effective not only as a remedy but also as a preventive by the transdermal administration of drugs. The application of such drugs by transdermal administration can produce the advantages of ease of administration and discontinuation, sustained release properties, and alleviation of adverse side-effects, etc., and thus it is especially useful for the treatment of angina pectoris which is the disease with unpredictable spasm.

Japanese Patent Publn. No. 52685/1985, corresponding U.S. Pat. No. 4,200,640 and corresponding DOS No. 27 14 713 disclose that N-(2-hydroxyethyl)nicotinamide nitrate (generically referred to hereafter as "Nicorandil") is useful for the treatment of various circulatory diseases, but do not suggest the preparations for transdermal administration.

As regards the preparations for transdermal administration of Nicorandil, Japanese Patent LOP Publn. No. 10513/1984 discloses those comprising Nicorandil and a polymer material formed on a flexible support, said polymer material having pressure-sensitive properties at ordinary temperature and having glass transition temperature adjusted to a temperature between −70° C. and −10° C. However, such preparations have suffered from the disadvantages of low solubility of Nicorandil in the polymer material with difficulty in releasing an effective amount of Nicorandil therefrom within a limited period of time, with the result of delayed exhibition of expected pharmacological activities of Nicorandil and difficulty in transdermal permeation of an effective amount of the active ingredient.

Under the circumstances mentioned above, it has been ardently desired to develop Nicorandil preparations for transdermal administration which are capable of exhibiting their pharmacological activities in an early stage of administration and which have sustained release property.

SUMMARY OF THE INVENTION

An object of the invention is to provide new Nicorandil containing external preparations which are excellent in initial release property and have sustained release property.

Another object of the invention is to provide a new mixed solvent for the transdermal formulas of Nicorandil.

The invention is based on the discovery that a formula of Nicorandil in a mixed solvent comprising an alcohol of 2 to 7 carbon atoms and an aliphatic ester having a molecular weight of at least 180 can provide Nicorandil with excellent solubility, release property and permeability to skin.

DETAILED DESCRIPTION OF THE INVENTION

According to this invention, there are provided external preparations which comprise as an active ingredient a formula of N-(2-hydrxyethyl)nicotinamide nitrate in a mixed solvent comprising an alcohol of 2 to 7 carbon atoms and an aliphatic ester having a molecular weight of at least 180.

This formula can be compounded with a base to formulate into such external preperations as ointment of pecia. The term "pecia" as used herein means a plaster applied to skin, having a paste containing drugs spread evenly on a uniform support, e.g., fabric, the back of which may be coated with a water-repellent film. Pecia is usually used in the form of tapes and patches. In addition thereto, the external preparations include any conventional preparations, for example, lotions, sprays, plasters, etc. The ointment has an advantage of ease of increase and decrease of drugs, and the pecia has an advantage of quantitative and continuous delivery of drugs. Therefore, these preparations can be applied suitably depending on sympton of the patient.

Nicorandil used as an active ingredient in the present invention is N-(2-hydroxyethyl)nicotinamide nitrate of the formula

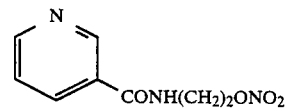

and is known to be effective as a vasodilator, particularly as a remedy for the treatment of angina pectoris as disclosed in Japanese Patent Publn. No. 52685/1985, corresponding DOS No. 27 14 713 and corresponding U.S. Pat. No. 4,200,640. The above-mentioned disclosures are hereby incorporated by reference.

The mixed solvent used in the present formulas comprise an alcohol of 2 to 7 carbon atoms and an aliphatic ester having a molecular weight of at least 180 which aid in the transdermal penetration of the active ingredient so that it is absorbed into the bloodstream.

Examples of the alcohols of 2 to 7 carbon atoms include, e.g., monohydric alcohols such as ethanol, isopropyl alcohol, butyl alcohol and benzyl alcohol; dihydric alcohols such as ethylene glycol, propylene glycol, diethylene glycol and trimethylene glycol; and polyhydric alcohols such as glycerin, erythritol, arabitol, xylitol, sorbitol and mannitol. From the viewpoint of irritability to skin and stability of the bases for external preparations, dihydric and polyhydric alcohols are preferable.

Examples of aliphatic esters having a molecular weight of at least 180 include, e.g., diethyl adipate, diisopropyl adipate, diethyl sebacate, dibutyl sebacate, ethyl laurate, glycol laurate, isoproply myristate, octyldodecyl myristate, isoproply palmitate, glycol palmitate, glycol stearate, decyl oleate, methyl arachidonate, etc.

For the external preparations, a combination of one or more alcohols and one or more esters can be used as a mixed solvent. The weight ratio of alcohols to esters in the mixed solvent is not specifically limited, but will generally range from 10:90 to 99:1 and preferably from 30:70 to 99:1.

The mixed solvents may further contain other solvents such as purified water, and known absorption accelerators (pyrrolidones, lecithin and higher fatty acids, etc.)

The proportion of Nicorandil component ranges from 0.5 to 100 parts by weight, preferably from 1 to 60 parts by weight, based on 100 parts by weight of the above-mentioned mixed solvent.

According to the conventional method, Nicorandil is suspended or dissolved in the solvent system containing the aforementioned mixed solvent to prepare a suspension or a solution. In this case, if necessary, there may be used suspending agents such as glycerol monostearate, polyoxyethylene sorbitan monostearate, polyoxyethylene hardened castor oil, etc.

The bases used in the present invention are not particularly limited so long as they are used for external preparations. Typical examples of the bases include gelatin, carboxy vinyl polymers, sodium polyacrylate, polyethylene glycol, white vaseline, stearyl alcohol, cetyl alcohol, carboxymethyl cellulose, methyl cellulose, hydroxypropyl cellulose, ethyl cellulose, hydroxyethyl cellulose, polyvinyl alcohol, polyvinyl pyrrolidone, polyvinyl chloride, vegetable and animal fats and oils, liquid paraffin and silicone resins.

With the bases mentioned above, there may be prepared according to the conventional method the external preparations, for example, ointment and pecia such as tapes and patches. In the case of the ointment as well as the pecia, the content of Nicorandil is not particularly limited, but it is usually 0.1–20%, preferably 0.5–10% by weight for the ointment. In applying the ointments to patients, an appropriate dose, preferably 20 mg–10 g once is applied between once and several times per day to a given portions of the patient, for example, the breast, abdomen or back.

When the pecia is applied to patients, about 1–100 cm$^2$ patch containing Nicorandil preferably at a loading concentration of 0.01–100 mg/cm$^2$ is applied to a given portions of the patient, e.g., the breast, abdomen or back. The patch is replaced once or twice a day or once every few days.

The dose and the number of times applied may be varied depending on the age and condition of the patient.

The present invention is illustrated below in more detail with reference to examples and test examples, but it should be construed that the invention is in no way limited thereto.

TEST EXAMPLE 1

The effects of the solvent compositions on the permeation of Nicorandil through the skin were studied using varied compositions of the solvent.

An abdominal skin of male hairless rat weighing about 150 g was excised under anesthesia and mounted on a 2-chamber diffusion cells having a diffusion effective area of 0.636 cm$^2$. To the corneum side of the skin were added 2 ml of Nicorandil suspensions in each of the solvents shown in Table 1, and to the corium side of the skin was added 2 ml of physiological saline. The cell was maintained at 37° C., and the physiological saline at the corium side of the skin was sampled with the lapse of time.

The amount of Nicorandil in the skin diffusion samples was quantified using a high pressure liquid chromatography (HPLC) in accordance with the method of Kamiyama et al mentioned in the Japanese reference, "Applied Pharmacology" 23(2) 261–266 (1982). The results are shown in Table 2.

As shown in Table 2, the amount of Nicorandil permeated through the skin was remarkably high in the case where the mixed solvents of the present invention were used.

Table 1

| Solvent composition No. | Composition of solvent (wt. ratio) | Solubility of Nicorandil (mg/ml, 37° C.) |
|---|---|---|
| 1 | Physiological saline | 23 |
| 2 | PG | 173 |
| 3 | IM | 3.7 |
| 4 | PG:IM (99:1) | 203 |
| 5 | PG:IM (99:5) | 197 |
| 6 | PG:IM (90:10) | 178 |
| 7 | PG:IM (75:25) | 155 |
| 8 | PG:IM (50:50) | 114 |
| 9 | PG:IM (10:90) | 18 |
| 10 | PG:DS (90:10) | 210 |
| 11 | EG:IP (90:10) | 165 |
| 12 | E:PW:ODM (45:45:10) | 310 |
| 13 | PG:E:PW:EL (30:30:30:10) | 286 |

PG = Propylene Glycol
DS = Diethyl Sebacate
IP = Isopropyl Palmitate
PW = Purified Water
EL = Ethyl Laurate
IM = Isopropyl Myristate
EG = Ethylene Glycol
E = Ethanol
ODM = Octyldodecyl Myristate

TABLE 2

Relationship between the amount of Nicorandil permeated through the skin and the time elapsed or the composition of solvent

| Solvent composition No. | Time elapsed (hr) and amount of Nicorandil permeated ($\mu$g/cm$^2$) | | | | |
|---|---|---|---|---|---|
| | 2 h | 4 h | 6 h | 8 h | 10 h |
| 1 | 20 | 49 | 77 | 107 | 140 |
| 2 | 15 | 60 | 125 | 214 | 300 |
| 3 | 59 | 252 | 491 | 758 | 1003 |
| 4 | 99 | 912 | 3180 | 6705 | 9569 |
| 5 | 158 | 1367 | 4551 | 9611 | 13300 |
| 6 | 449 | 3272 | 7187 | 12300 | 15778 |
| 7 | 401 | 1932 | 4758 | 7764 | 9002 |
| 8 | 534 | 2344 | 5575 | 9275 | 13200 |
| 9 | 376 | 994 | 1653 | 2406 | 3284 |
| 10 | 33 | 287 | 1776 | 6613 | 12947 |
| 11 | 125 | 603 | 1186 | 2142 | 3404 |
| 12 | 219 | 896 | 1652 | 2334 | 3352 |
| 13 | 1383 | 3339 | 6918 | 9905 | 14331 |

EXAMPLE 1

Four grams of Nicorandil were suspended in a mixed solvent comprising 10 g of propylene glycol and 0.5 g of diethyl sebacate. The suspension was added to a mixture of 83 g of white vaseline and 2.5 g of glyceryl monostearate (Nikkol MGS-B, a product of Nikko Chemicals Co., Ltd) melted at about 60° C., and the resulting mixture was kneaded to prepare an ointment.

EXAMPLE 2

Five grams of Nicorandil were suspended in a mixed solvent comprising 13 g of propylene glycol and 2 g of ethyl laurate. The suspension was added to a mixture of 30 g of purified water and polyoxyethylene hardened castor oil (Nikkol HCO-60, a product of Nikko Chemicals Co., Ltd.) heated at about 70° C., and the resulting mixture was stirred to prepare a Nicorandil containing liquid.

Subsequently, this Nicorandil containing liquid was added with stirring to a mixture of 25 g white vaseline, 20 g of stearyl alcohol and 1 g of glyceryl monostearate (Nikkol MGS-B) melted at about 75° C., and the resulting mixture was cooled to room temperature to prepare an ointment.

EXAMPLE 3

Two grams of Nicorandil were dissolved in a mixed solvent comprising 29 g of ethylene glycol and 1 g of isoproply palmitate. The solution was added to a solution of 1 g of a carboxyvinyl polymer (Carbopole 934, a product of Goodrich Co., Ltd.) in 14.5 g of purified water and 50 g of ethylene glycol, and the mixture was stirred. Finally, the mixture obtained was charged with 2.5 g of ETHOMEEN C-25 (a product of Lion-Armak Co., Ltd.), and the resulting mixture was kneaded to prepare an ointment.

EXAMPLE 4

Five grams of Nicorandil were dissolved in a mixed solvent comprising 35 g of propylene glycol, 2 g of isopropyl myristate and 3 g of octyldodecyl myristate. The solution was added to a mixture of 30 g of stearyl alcohol, 5 g of stearic acid and 20 g of PEG 400 melted at about 70° C., and the mixture was cooled with stirring to room temperature to prepare an ointment.

EXAMPLE 5

Five grams of Nicorandil were suspended in a mixed solvent comprising 13.5 g of propylene glycol and 1.5 g of isopropyl myristate to prepare a Nicorandil suspension. Separately, 4 g of gelatin were dissolved under heat in 20 g of purified water, and the solution was charged successively with 27 g of glycerin, 1 g of polyoxyethylene monostearate (Tween 60), 18 g of kaolin, 3 g of carboxymethyl cellulose and 5 g of polyvinyl pyrrolidone. To this mixture were added the Nicorandil suspension as prepared above and 2 g of sodium polyacrylate, and the resulting mixture was homogeneously kneaded to prepare a base. One hundred grams of the kneaded product were spread on a 100 cm² cotton flannel to prepare a pecia. This pecia was cut into a circular piece of 2.5 cm in diameter, which was used for the following transdermal permeation test.

EXAMPLE 6

One gram of Nicorandil was dissolved in a mixed solvent comprising 20 g of glycerin and 3 g of dibutyl sebacate. The solution was charged with 5 g of sodium polyacrylate, 0.5 g of hydroxypropylmethyl cellulose, 0.3 g of magnesium metasilicate aluminate, 0.3 g of calcium hydrogenphosphate, 0.1 g of butylparaben and 0.1 g of methylparaben, and mixed. To this mixture were added an emulsion of 30 g of a 10% aqueous polyacrylic acid solution, 3 g of SEFSOL 318 (a product of Nikko Chemical Co., Ltd.) and 0.5 g of polyoxyethylene sorbitan monooleate in 20 g of purified water, and then added a solution of 0.05 g of tartaric acid and 0.03 g of EDTA in purified water to make a total volume of 100 g. The resultant mixture was homogenously kneaded. One hundred grams of the kneaded product of were spread on an unwoven fabric of 20 cm×40 cm to prepare a pecia. This pecia was cut into a circular piece of 2.5 cm in diameter, which was used for following transdermal permeation test.

TEST EXAMPLE 2

The transdermal permeation of Nicorandil was studied using hairless rat.

To an abdominal skin of male hairless rat weighing about 150 g was attached a cylindrical glass cell of 2.5 cm in diameter, in which 2 g each of the ointments prepared in Examples 1–4 was charged and the cell was sealed with a paraffin film.

The pecia prepared in Examples 5 and 6 were individually fixed onto an aluminum laminate and sticked on the abdomen of the rat and fixed thereto with a urethane adhesive sheet.

As a comparative example, an ointment was prepared by adding 5 g Nicorandil to a mixture of 92.5 g of white waseline and 2.5 g of glyceryl monostearate (Nikkol MGS-B) melted at about 60° C. and thoroughly kneading the mixture. The ointment was administered to the hairless rat in the same manner as mentioned above.

3, 6 and 9 hours after the application, 1 cc of blood was collected from the jugular vein of rat, and the plasma Nicorandcil levels were determined with HPLC. The results are shown in Table 3.

TABLE 3

Plasma Nicorandil levels of hairless rat, 3, 6 and 9 hrs after application of Nicorandil external preparations

| Example No. | Plasma Nicorandil levels (μg/ml) | | |
|---|---|---|---|
| | 3 hrs. | 6 hrs. | 9 hrs. |
| 1 | 0.40 | 0.70 | 1.26 |
| 2 | 0.32 | 0.88 | 0.75 |
| 3 | 1.10 | 1.86 | 2.52 |
| 4 | 0.12 | 1.05 | 1.33 |
| 5 | 0.25 | 0.91 | 0.88 |
| 6 | 0.22 | 0.35 | 0.48 |
| Comparative Example | 0 | 0.02 | 0.03 |

As shown in Table 3, the Nicorandil external; preparations exhibited extremely high plasma Nicorandil levels as compared with that of Comparative Example.

In accordance with the present invention, as detailed hereinbefore, there can be prepared the Nicorandil external preparations useful for the treatment of angina pectoris which have excellent initial release of the active ingredient and further have sustained release property.

What is claimed is:

1. An external preparation which comprises as an active ingredient from 0.5 to 100 parts by weight of a formula of N-(2-hydroxyethyl) nicotinamide nitrate in a mixed solvent consisting essentially of an alcohol of 2 to 7 carbon atoms and an aliphatic ester having a molecular weight of at least 180, and an external preparataion base, the weight ratio of the alcohol to the ester being in the range of from 10:90 to 99:1, the alcohol being selected from the group consisting of monohydric alcohols, dihydric alcohols and polyhydric alcohols, and the ester being selected from the group consisting of diethyl adipate, diisopropyl adipate, diethyl sebacate, dibutyl sebacate, ethyl laurate, glycol laurate, isopropyl myristate, octyldodecyl myristate, isopropyl palmitate, glycol palmitate, glycol stearate, decyl oleate and methyl arachidonate.

2. The preparation of claim 1 wherein the monohydric alcohols are selected from the group consisting of ethanol, isopropyl alcohol, butyl alcohol and benzyl alcohol.

3. The preparation of claim 1 wherein the dihydric alcohols are selected from the group consisting of ethylene glycol, propylene glycol, diethylene glycol and trimethylene glycol.

4. The preparation of claim 1 wherein the polyhydric alcohols are selected from the group consisting of glycerin, erythritol, arabitol, xylitol, sorbitol and mannitol.

5. The preparation of claim 1 wherein the mixed solvent contains further other solvents and known absorption accelerators.

6. The preparation of claim 1 which is in the form of an ointment and a pecia.

7. The preparation of claim 6 wherein the pecia is used in the form of tapes and patches.

* * * * *